(12) United States Patent
Qi et al.

(10) Patent No.: US 9,863,922 B2
(45) Date of Patent: Jan. 9, 2018

(54) $NO_x$ SENSOR CALIBRATION AND APPLICATION IN LEAN $NO_x$ TRAP AFTERTREAT SYSTEMS

(71) Applicant: GM GLOBAL TECHNOLOGY OPERATIONS LLC, Detroit, MI (US)

(72) Inventors: Gongshin Qi, Troy, MI (US); Kevin L. Perry, Fraser, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 472 days.

(21) Appl. No.: 14/527,412

(22) Filed: Oct. 29, 2014

(65) Prior Publication Data
US 2016/0123945 A1  May 5, 2016

(51) Int. Cl.
*G01N 33/00* (2006.01)
*F01N 9/00* (2006.01)
*F01N 3/08* (2006.01)
*B01D 53/30* (2006.01)
*B01D 53/94* (2006.01)

(52) U.S. Cl.
CPC ......... *G01N 33/0037* (2013.01); *B01D 53/30* (2013.01); *B01D 53/9495* (2013.01); *F01N 3/0842* (2013.01); *F01N 9/00* (2013.01); *B01D 53/9431* (2013.01); *B01D 2257/404* (2013.01); *B01D 2258/018* (2013.01); *F01N 2560/026* (2013.01); *F01N 2560/14* (2013.01); *Y02T 10/24* (2013.01); *Y02T 10/47* (2013.01)

(58) Field of Classification Search
CPC ............ G01N 33/0037; B01D 53/9495; B01D 53/9431; B01D 2258/018; F01N 3/0842; F01N 9/00; F01N 2560/026; F01N 2560/14
USPC ........................................................ 73/23.31
See application file for complete search history.

(56) References Cited

U.S. PATENT DOCUMENTS

| | | | |
|---|---|---|---|
| 6,820,597 B1 * | 11/2004 | Cullen | F02D 17/02 123/516 |
| 6,823,662 B1 * | 11/2004 | Yamamoto | B01D 53/8631 123/3 |
| 2009/0000274 A1 * | 1/2009 | Stroh | F01N 3/0814 60/274 |
| 2014/0157760 A1 * | 6/2014 | Tufail | F01N 3/208 60/274 |

* cited by examiner

Primary Examiner — Lisa Caputo
Assistant Examiner — Nathaniel T Woodward

(57) ABSTRACT

An aftertreatment system utilizes chemical reactions to treat an exhaust gas flow. A system for aftertreatment of the exhaust gas flow includes a NOx sensor configured to monitor within the exhaust gas flow one of a lambda value and a NOx concentration value and a computerized processor device configured to calibrate the monitored value for presence of one of $NH_3$, $H_2$, and hydrocarbons. In one embodiment, the system further includes a pair of NOx sensors, each monitoring both a lambda value and a NOx concentration value. In another embodiment, the system controls the aftertreatment based upon the calibrated values.

14 Claims, 3 Drawing Sheets

NO$_x$ SENSOR CALIBRATION AND APPLICATION IN LEAN NO$_x$ TRAP AFTERTREAT SYSTEMS

TECHNICAL FIELD

This disclosure is related to control of aftertreatment of NOx emissions in internal combustion engines.

BACKGROUND

The statements in this section merely provide background information related to the present disclosure and may not constitute prior art.

Emissions control is one factor in engine design and engine control. One particular emission, NOx, is a known by-product of combustion. NOx is created by nitrogen and oxygen molecules present in engine intake air disassociating in the high temperatures of combustion, and rates of NOx creation include known relationships to the combustion process, for example, with higher rates of NOx creation being associated with higher combustion temperatures and longer exposure of air molecules to the higher temperatures.

NOx molecules, once created in the combustion chamber, can be converted back into nitrogen and H$_2$O molecules in exemplary devices known in the art within the broader category of aftertreatment devices. Aftertreatment devices are known, for instance, utilizing chemical reactions to treat an exhaust gas flow. One exemplary device includes a selective catalytic reduction device (SCR). An SCR utilizes a reductant capable of reacting with NOx to treat the NOx. One exemplary reductant is ammonia derived from urea injection. A number of alternative reductants are known in the art. Ammonia stored on a catalyst bed within the SCR reacts with and treats NOx.

According to one embodiment of aftertreatment system operation, an engine can be operated in a stoichiometry operating mode or lean combustion mode. Such operation produces NOx and creates conditions in the exhaust gas flow that are known in the art to be unfavorable to treatment of the NOx while the operation remains in the lean combustion mode. A lean NOx trap (LNT) can be used for during such operation to store NOx within the LNT until a purge cycle under stoichiometric or rich combustion can occur to create conditions favorable to treatment of the stored NOx.

SUMMARY

An aftertreatment system utilizes chemical reactions to treat an exhaust gas flow. A system for aftertreatment of the exhaust gas flow includes a NOx sensor configured to monitor within the exhaust gas flow one of a lambda value and a NOx concentration value and a computerized processor device configured to calibrate the monitored value for presence of one of NH$_3$, H$_2$, and hydrocarbons. In one embodiment, the system further includes a pair of NOx sensors, each monitoring both a lambda value and a NOx concentration value. In another embodiment, the system controls the aftertreatment based upon the calibrated values.

BRIEF DESCRIPTION OF THE DRAWINGS

One or more embodiments will now be described, by way of example, with reference to the accompanying drawings, in which.

DETAILED DESCRIPTION

Figure 1:
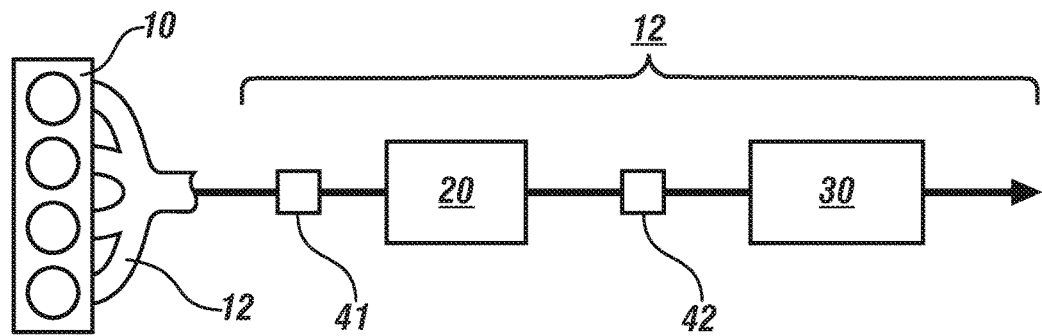
FIG. 1 illustrates an exemplary aftertreatment system treating an exhaust gas flow from an engine, in accordance with the present disclosure.

A NOx sensor can be used to monitor how much NOx is within the exhaust gas flow. Accurate tracking of NOx presence within the exhaust gas flow enables systems on the vehicle to utilize an lean NOx trap (LNT) during efficient lean operation of the engine and schedule purge cycles as needed. Advanced LNT aftertreatment architectures (LNT/ selective catalytic reduction coated diesel particulate filter (SCRF)) need to accurately quantify NOx values and ammonia generated during the LNT regeneration events.

Known LNT control and diagnostics are mainly based on the information coming from the wide band lambda sensors (in some embodiments, taking the form of a pair of universal exhaust gas oxygen sensors (UEGO)) located both upstream and downstream the catalyst. According to one embodiment, a NO$_x$ sensor could be applied to replace the UEGO sensor to decrease calibration workload since the NO$_x$ sensor can measure both NO$_x$ concentration and lambda value (a measure of the air to fuel ratio known in the art) simultaneously. Calibration to adjust for the behavior of NO$_x$ sensor is necessary for LNT control in order to understand how much the measurements are reliable and accurate in an exhaust gas mixture, especially during the LNT regeneration period, and to understand the limitations of the NO$_x$ sensor. A system and method are disclosed utilizing a NOx sensor to provide both NOx readings and lambda readings in an exhaust gas flow along with control based upon a cross sensitivity function with typical gases (H$_2$, CO, NH$_3$ and hydrocarbons (HCs)) produced by rich combustion and LNT catalysts. Such a system and method to correct NOx sensor sensitivity can provide improved LNT regeneration control and strategies to differentiate between NOx and ammonia during LNT regeneration events.

NOx sensor readings used to determine NOx presence in the exhaust gas flow or NOx concentration include cross sensitivity with elements of the exhaust gas flow, in particular with ammonia. In operation without NH$_3$ or engine operation in a zone where ammonia production does not occur, a high accuracy range can be defined for a NOx sensor for all the other elements excluding NH$_3$ (including +/−15 ppm under 100 ppm and +/−15% above 100 ppm.) After NH$_3$, the HC and H$_2$ presence/concentrations have the next greatest impacts on the cross sensitivity.

NOx sensor readings used to determine lambda also include cross sensitivity with elements of the exhaust gas flow. The lambda reading shows significant cross sensitivity with respect to H$_2$. The characteristic is shifted to the richer side and the deviation of the lambda sensor output/reading is up to 6% when $H_2$ concentration varied from 0-1%.

The lambda reading shows a small cross sensitivity with respect to HCs, the deviation is less than 0.5% for the HC concentration from 0 to 5000 ppm ($C_3$). The lambda reading does not show a cross sensitivity with respect to $NH_3$. In order to provide accurate readings of both NOx and lambda values, it is important to determine the cross sensitivity function with typical gas produced by a rich combustion mode, such as HCs, $NH_3$ and $H_2$.

NOx and ammonia could be differentiated and NOx readings adjusted based on calibrated lambda values during LNT regeneration events. NOx sensor readings are attributed to NOx spike if the lambda reading indicates operation lean of or a lambda value higher than the stoichiometric point. If the lambda value indicates operation rich of or a lambda value lower than the stoichiometric point, NOx sensor readings can be attributed to or adjusted based upon $NH_3$ generated from the LNT device during the rich event.

Referring now to the drawings, wherein the showings are for the purpose of illustrating certain exemplary embodiments only and not for the purpose of limiting the same, FIG. 1 illustrates an exemplary aftertreatment system treating an exhaust gas flow from an engine. Exemplary internal combustion engine 10 is illustrated, combusting a fuel air mixture to generate mechanical power, and as a result of the combustion, an exhaust gas flow including chemical byproducts of the combustion process is forced through exhaust aftertreatment system 12. Exemplary aftertreatment system 12 includes a LNT device 20, an SCRF device 30. A NOx sensor 41 is illustrated upstream of LNT device 20, and a second NOx sensor 42 is illustrated downstream of LNT device 20. Readings from NOx sensors 41 and 42 can be used both to diagnose and control NOx contained within LNT device 20 and to diagnose an actual air to fuel ratio. LNT device 20 is illustrated separated from engine 10 and a connected exhaust manifold 12. It will be appreciated that the LNT device 20 can be close coupled with the exhaust manifold in accordance with the present disclosure. The arrangement of devices within aftertreatment system 12 is exemplary and non-limiting, and other configurations and other devices utilizing ammonia oxidation catalysts can similarly be arranged and utilized.

NOx sensors 41 and 42 are used to monitor NOx flowing into LNT device 20 and NOx flowing out of LNT device 20. A difference between sensor readings from the two can be used to approximate a change in NOx stored in the LNT device 20. In other aftertreatment systems, for example, replacing LNT device 20 with a three way catalyst and SCRF device 30 with a standard SCR device, a single NOx sensor can be used to monitor and control conditions within the aftertreatment system.

Figure 2:
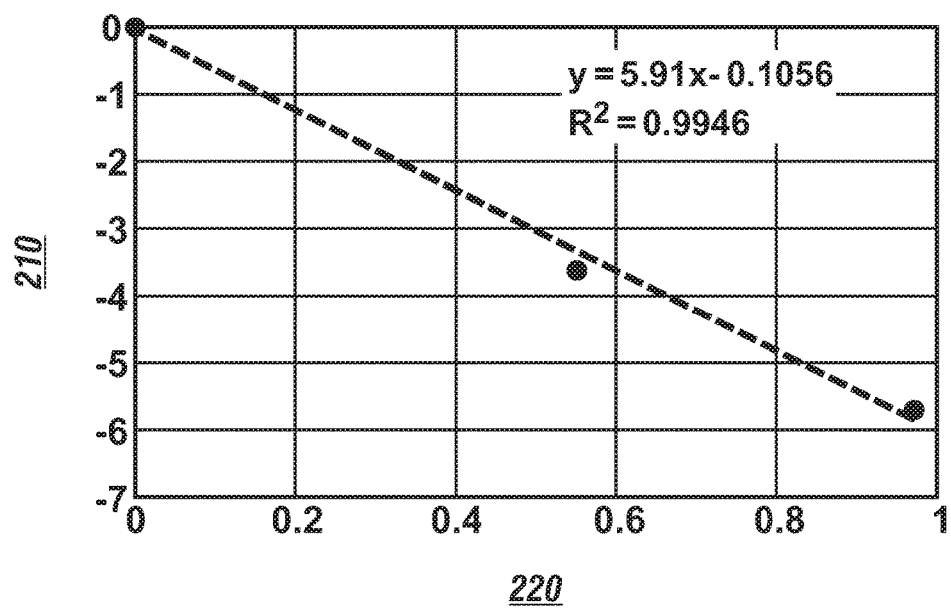
FIG. 2 illustrates exemplary cross sensitivity between H$_2$ concentration in the exhaust gas flow and lambda variation, in accordance with the present disclosure.

FIG. 2 illustrates exemplary cross sensitivity between $H_2$ concentration (%) in the exhaust gas flow and lambda variation (%). The horizontal axis (220) shows increasing $H_2$ concentration in the exhaust gas flow. The vertical axis (210) shows variation in lambda readings. Increasing presence of $H_2$ in the exhaust gas flow causes lambda sensor signal shifts to the richer side. NOx sensor lambda reading shifts to the richer side in the presence of $H_2$ and the deviation can be as much as 6% with $H_2$ concentration varying from 0-1%. Testing has shown that the deviation can be as much as 10% with $H_2$ concentration varying from 0-2%.

Figure 3:
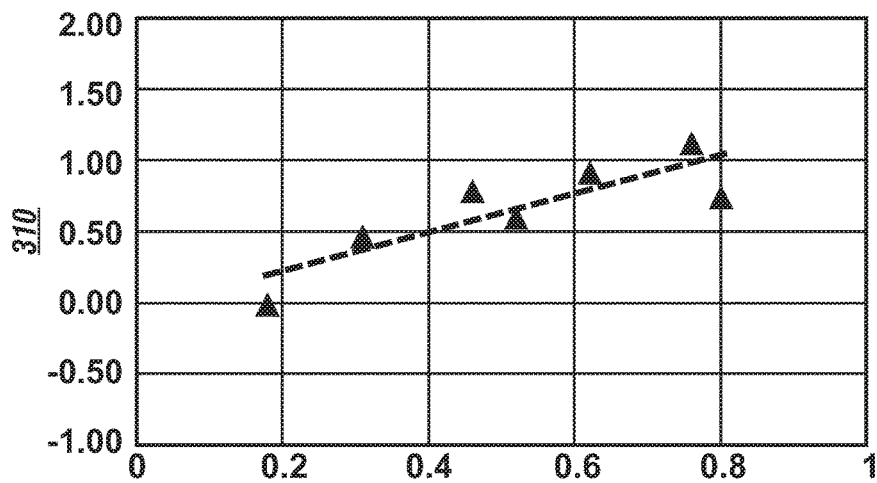
FIG. 3 illustrates exemplary cross sensitivity between hydrocarbon concentration in the exhaust gas flow and lambda variation, in accordance with the present disclosure.

FIG. 3 illustrates exemplary cross sensitivity between hydrocarbon concentration (C3H6/C3H8 (ppm)) in the exhaust gas flow and lambda variation (%). The horizontal axis (320) shows increasing hydrocarbon concentration in the exhaust gas flow. The vertical axis (310) shows variation in lambda readings. Lambda sensor shows a small cross sensitivity with respect to HCs, with a deviation less than 1% for HC concentration from 0 to 5000 ppm ($C_3$ based).

Testing shows that lambda sensor readings do not show a cross sensitivity with respect to $NH_3$.

Because presence of hydrocarbons and $NH_3$ show little or no cross sensitivity with lambda sensor readings on a NOx sensor, a method to correct NOx sensor reading for cross sensitivity with component gases in the exhaust gas flow can include an adjustment for $H_2$ presence while making no adjustment for presence of hydrocarbons and ammonia. A correction factor based on the cross sensitivity with respect to $H_2$ can be used for lambda sensor reading adjustment during LNT regeneration events.

Figure 4:
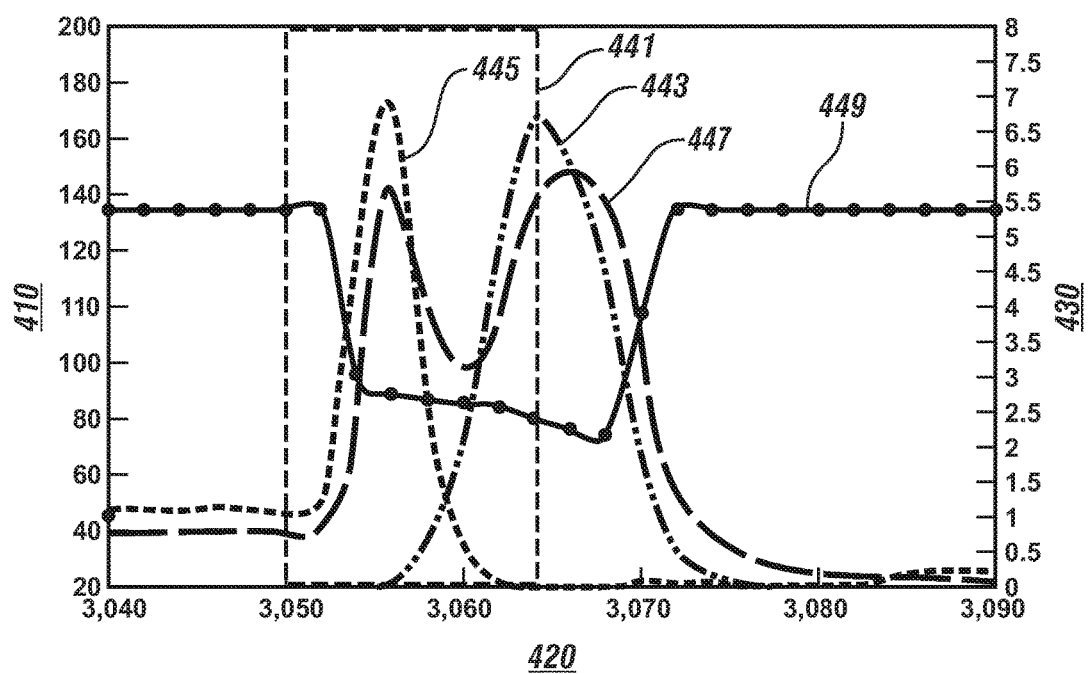
FIG. 4 illustrates cross sensitivity of NOx readings from a NOx sensor based upon a controlled lambda value and corresponding NH$_3$ values in the monitored exhaust gas flow, in accordance with the present disclosure.

FIG. 4 illustrates cross sensitivity of NOx readings from a NOx sensor based upon a controlled lambda value and corresponding $NH_3$ values in the monitored exhaust gas flow. A left vertical axis (410) illustrates concentration values (ppm) for $NH_3$ and NOx through the test period. The right vertical axis (430) illustrates NOx sensor voltage through the test period. The horizontal axis (420) illustrates time progression through the test period in seconds. The dashed horizontal line illustrates a stoichiometric lambda value. Dashed vertical lines (441) illustrate times at which engine valve control strategies are adjusted to initiate lambda changes through the test period. Lambda (449) starts through an initial period at the left of the figure at a high value corresponding to lean operation of the engine. Through this initial period, NH3 presence value (443) in the exhaust gas flow remains negligible. A nearly constant NOx presence value (445) is illustrated, and a NOx sensor value (447) corresponding to a NOx reading closely tracks the NOx presence value (445). As the valving strategy is changed the first time, the lambda value (449) decreases rapidly toward the stoichiometric value. NOx presence increases rapidly and the NOx sensor value tracks the raising NOx presence value closely. The NOx presence value reaches a peak and begins to decline, and the NOx sensor value closely tracks the peak and initial decline of the NOx presence value. As lambda crosses the stoichiometric line and continues to decline, $NH_3$ presence begins to rise and the NOx value quickly decreases. As the $NH_3$ value rises, the NOx sensor value ceases to closely track the NOx value and begins to act as an approximation of a sum of the NOx value and $NH_3$ value. As the NOx value approaches zero, the NOx sensor value roughly tracks the $NH_3$ value. As the valving strategy is changed the second time, the lambda value peaks at a low value and then rises back to the original high value indicating lean operation. The $NH_3$ value quickly drops corresponding to typical low $NH_3$ presence in lean operation. The values illustrated in FIG. 4 provide illustration of an exemplary control method, whereby NOx sensor values can be used to directly approximate NOx presence values when lambda is lean of stoichiometry. When the lambda value is rich of stoichiometry, the NOx sensor value can be used to approximate $NH_3$ presence.

Processes to monitor sensor inputs including readings from the NOx sensor can be operated as an automated, computerized process within a processing device such as an engine controller or aftertreatment control module. Controllers, modules, and processing devices can be used to indicate a single or multiple physical devices with functionality split between the devices according to methods known in the art.

Control process and methods disclosed herein can be operated within a computerized processing device within a controller or module. The processing device can be a computerized device operating according to configurations and methods known in the art and can include memory, e.g., read only memory (ROM) and random access memory (RAM), storing processor-executable instructions and one or more processors that execute the processor-executable instructions. In embodiments where the processing device includes two or more processors, the processors can operate in a parallel or distributed manner. Programming can be stored in any memory device known in the art such as flash memory.

Figure 5:
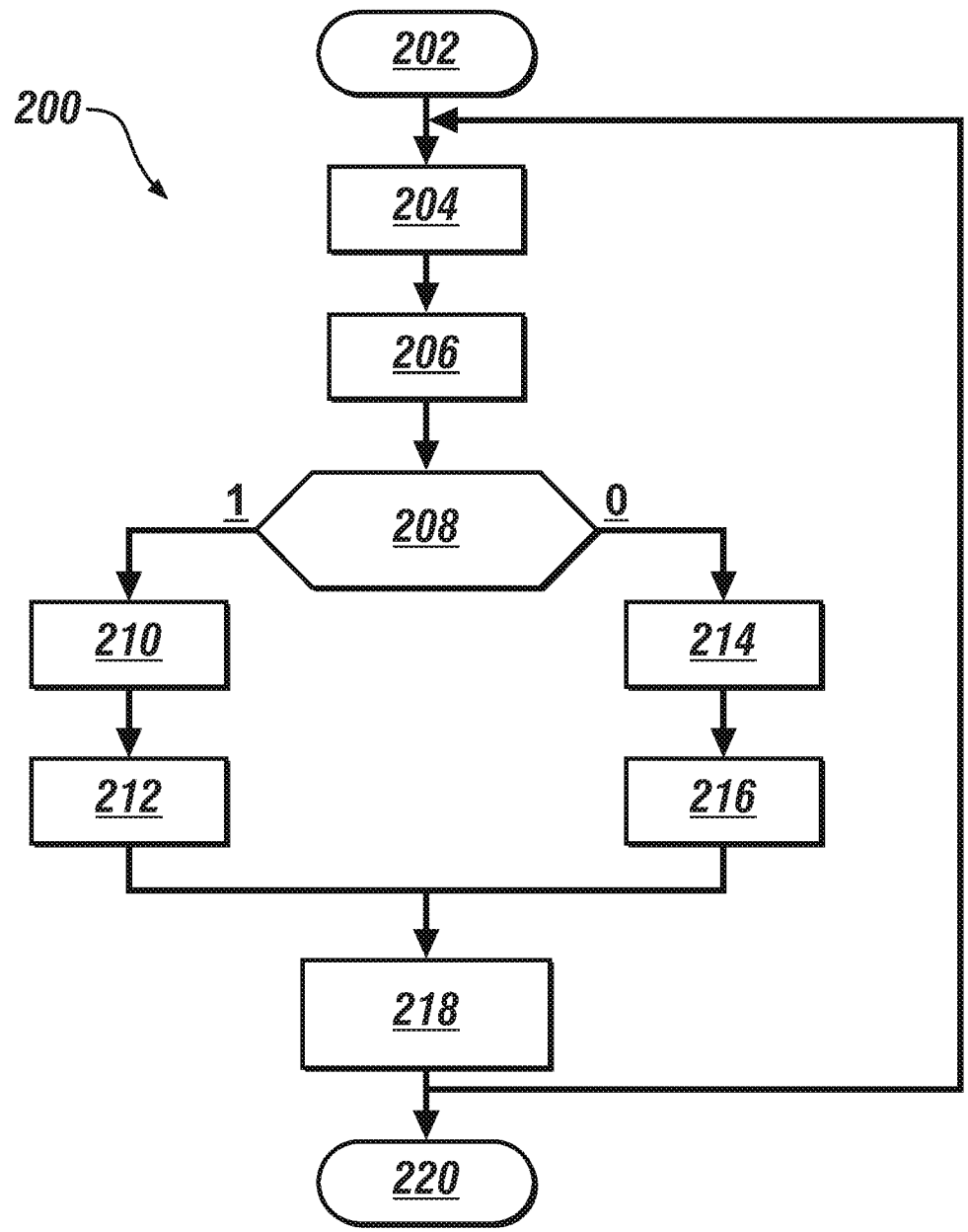
FIG. 5 is a flowchart illustrating an exemplary control process utilizing the system and method disclosed herein to control an aftertreatment system through evaluation and calibration of NOx sensor signals, in accordance with the present disclosure.

FIG. 5 is a flowchart illustrating an exemplary control process utilizing the system and method disclosed herein to control an aftertreatment system through evaluation and calibration of NOx sensor signals. The process steps include the following.

| STEP NO. | PROCESS STEP |
|---|---|
| 202 | START |
| 204 | MONITOR NOx SENSOR SIGNAL FOR LAMBDA VALUE |
| 206 | ESTIMATE LAMBDA VALUE BASED UPON CALIBDATED $H_2$ ADJUSTMENT |
| 208 | DETERIMINE: IS THE ESTIMATED LAMBDA VALUE LEAN OF STOICHIMETRY? |
| 210 | MONITOR NOx SENSOR SIGNAL FOR NOx PRESENCE VALUE |
| 212 | ESTIMATE NOx PRESENCE BASED UPON THE MONITORED NOx SENSOR SIGNAL |
| 214 | MONITOR NOx SENSOR SIGNAL FOR $NH_3$ PRESENCE VALUE |
| 216 | ESTIMATE $NH_3$ PRESENCE BASED UPON THE MONITORED NOx SENSOR SIGNAL |
| 218 | CONTROL THE AFTERTREATMENT SYSTEM BASED UPON THE ESTIMATED VALUE |
| 220 | END THE PROCESS UPON ENGINE SHUTDOWN |

Process 200 of FIG. 5 starts upon engine startup. In steps 204 and 206, the process utilizes the disclosed NOx sensor to determine a lambda value including an adjustment for $H_2$ present in the exhaust gas flow. At step 208, the process determines whether the adjusted lambda value indicates lean or rich operation of the engine. If the operation is determined to be lean, the process uses steps 210 and 212 to determine NOx presence based upon the NOx sensor value. If the operation is determined to be rich, the process uses steps 214 and 216 to determine $NH_3$ presence based upon the NOx sensor value. At step 218, the process controls the aftertreatment system and any other relevant systems based upon the determined values. The process repeats to step 204 until engine shut off, where the process ends at step 220.

The flowchart and block diagrams in the flow diagrams illustrate the architecture, functionality, and operation of possible implementations of systems, processes, and computer program products according to various embodiments of the present disclosure. In this regard, each block in the flowchart or block diagrams may represent a module, segment, or portion of code, which comprises one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable medium that can direct a computer or other programmable data processing device to function in a particular manner, such that the instructions stored in the computer-readable medium produce an article of manufacture including instruction means which implement the function/act specified in the flowchart and/or block diagram block or blocks.

A system and method disclosed herein can utilize a pair of NOx sensors located upstream and downstream of an LNT device to control the aftertreatment system and the related purge cycles of the LNT device. Other embodiments including a single NOx sensor are envisioned. In one embodiment, the NOx sensor can be used to monitor both lambda and NOx presence or NOx concentration in the exhaust gas flow, wherein both the lambda value and the NOx concentration value are calibrated or adjusted for exhaust gas components such as $NH_3$, $H_2$, and HC. In other embodiments, the NOx sensor can be used to monitor one of lambda value and the NOx concentration value, wherein the monitored value is calibrated or adjusted for exhaust gas components such as $NH_3$, $H_2$, and HC. A number of variations of the use of a NOx sensor including calibrated sensor readings as disclosed herein are envisioned, and the disclosure is not intended to be limited to the particular exemplary embodiments of the disclosure.

The disclosure has described certain preferred embodiments and modifications thereto. Further modifications and alterations may occur to others upon reading and understanding the specification. Therefore, it is intended that the disclosure not be limited to the particular embodiment(s) disclosed as the best mode contemplated for carrying out this disclosure, but that the disclosure will include all embodiments falling within the scope of the appended claims.

The invention claimed is:

1. A system for aftertreatment of an exhaust gas flow, the system comprising:
a NOx sensor monitoring the exhaust gas flow and providing a lambda reading and a NOx reading; and
a computerized processor device selectively attributing the NOx reading to the presence of NOx when the lambda reading indicates lean exhaust gas flow and to the presence of $NH_3$ when the lambda reading indicates rich exhaust gas flow;
wherein the computerized processor device is further configured to control an aftertreatment system based upon the NOx reading.

2. The system of claim 1, wherein the computerized processor device calibrates the lambda reading and the NOx reading for presence of $NH_3$, $H_2$, and hydrocarbons.

3. The system of claim 1, wherein the computerized processor device calibrates the lambda reading for the presence of $H_2$.

4. The system of claim 1, wherein the computerized processor device calibrates the NOx reading for the presence of $NH_3$.

5. The system of claim 1, wherein the NOx sensor comprises a first NOx sensor; said system further comprising a second NOx sensor monitoring the exhaust gas flow at a different location than the first NOx sensor.

6. The system of claim 5, wherein the first NOx sensor is located upstream of a lean NOx trap device; and
wherein the second NOx sensor is located downstream of the lean NOx trap device.

7. The system of claim 1, further comprising a lean NOx trap device receiving the exhaust gas flow, wherein the computerized processor device utilizes the lambda and NOx readings to control a purge cycle for the lean NOx trap device.

8. The system of claim 7, further comprising a selective catalytic reduction coated diesel particulate filter located downstream of the NOx sensor.

9. The system of claim 1, wherein the NOx sensor is located upstream of a lean NOx trap device.

10. The system of claim 1, wherein the NOx sensor is located downstream of a lean NOx trap device.

11. A system for aftertreatment of an exhaust gas flow, the system comprising:
- a NOx sensor configured to monitor within the exhaust gas flow a lambda value and a NOx concentration value; and
- a computerized processor device, configured to calibrate the lambda value and the NOx concentration value for presence of one of $NH_3$, $H_2$, and hydrocarbons;
- wherein the computerized processor device calibrating the NOx concentration value comprises the computerized processor device attributing readings of the NOx sensor to one of NOx presence and $NH_3$ presence based upon the lambda value; and
- wherein the computerized processor device is further configured to control an aftertreatment system based upon the NOx reading.

12. The system of claim 11, wherein the computerized processor device attributing readings of the NOx sensor to one of NOx presence and $NH_3$ presence comprises, if the lambda value indicates lean operation, attributing the readings to NOx presence, and, if the lambda value indicates rich operation, attributing the readings to $NH_3$ presence.

13. A system for aftertreatment of an exhaust gas flow, the system comprising:
- a lean NOx trap device trapping NOx during lean operation of an engine;
- a first NOx sensor located upstream of the lean NOx trap device and monitoring the exhaust gas flow to providing a first lambda reading and a first NOx reading;
- a second NOx sensor located downstream of the lean NOx trap device and monitoring the exhaust gas flow to provide a second lambda reading and a second NOx reading; and
- a computerized processor device selectively attributing the respective NOx reading to the presence of NOx when the corresponding lambda reading indicates lean exhaust gas flow and to the presence of $NH_3$ when the corresponding lambda reading indicates rich exhaust gas flow;
- wherein the computerized processor device is further configured to control an aftertreatment system based upon the NOx reading.

14. A method for controlling aftertreatment of an exhaust gas flow, the method comprising:
- within a computerized processor device,
    - monitoring a first NOx sensor located upstream of a lean NOx trap device;
    - determining a first calibrated lambda reading from the first NOx sensor;
    - determining a first calibrated NOx reading from the first NOx sensor;
    - monitoring a second NOx sensor located downstream of a lean NOx trap device;
    - determining a second calibrated lambda reading from the second NOx sensor;
    - determining a second calibrated NOx reading from the second NOx sensor;
    - selectively attributing the respective NOx reading to the presence of NOx when the corresponding lambda reading indicates lean exhaust gas flow and to the presence of $NH_3$ when the corresponding lambda reading indicates rich exhaust gas flow; and
    - controlling a purge cycle of the lean NOx trap based upon the determined readings.

* * * * *